United States Patent [19]

Dobson et al.

[11] Patent Number: 4,912,260

[45] Date of Patent: Mar. 27, 1990

[54] PROCESS FOR THE PRODUCTION OF AMINES

[75] Inventors: Ian D. Dobson, Keyingham, England; Werner A. Lidy, Collonge-Bellerive, Switzerland; Peter S. Williams, Hull, England

[73] Assignee: BP Chemicals Limited, London, England

[21] Appl. No.: 170,827

[22] Filed: Mar. 21, 1988

[30] Foreign Application Priority Data

Mar. 26, 1987 [GB] United Kingdom ............... 8707304

[51] Int. Cl.$^4$ ............................................. C07C 63/14
[52] U.S. Cl. .................................................. 564/480
[58] Field of Search ........................................ 564/480

[56] References Cited

U.S. PATENT DOCUMENTS

| 2,848,495 | 8/1958 | Villemey | 564/480 |
| 3,278,598 | 10/1966 | Markiewitz | 564/480 |
| 4,495,369 | 1/1985 | Werner et al. | 564/480 |

*Primary Examiner*—Richard L. Raymond
*Assistant Examiner*—Raymond Covington
*Attorney, Agent, or Firm*—Brooks Haidt Haffner & Delahunty

[57] ABSTRACT

Amines are produced by reacting at elevated temperature a first reactant which is either an alcohol, an aldehyde or a ketone with a second reactant which is either ammonia, a primary or secondary amine or a nitrile in the presence as catalyst of a composition comprising (i) nickel, (ii) ruthenium, and (iii) at least one other transition metal selected from either the second or third row transition metals, for example palladium, rhenium or iridium.

13 Claims, No Drawings

PROCESS FOR THE PRODUCTION OF AMINES

The present invention relates generally to reductive amination, that is the reaction of either an alcohol, an aldehyde or a ketone with either ammonia or an amine or a nitrile in the presence of a catalyst to give an amine as the product, and in particular to the use of an improved catalyst composition in reductive amination reactions.

Reductive amination is a well-known reaction, which over the years has given rise to a large number of patents, the majority of them being devoted to catalysts for use in the reaction. Most of the prior art catalyst systems are based on either nickel or cobalt. In most examples of reductive amination problems arise from the co-production of unwanted by-products, for example in the case of the reaction between an alcohol and ammonia by the following reaction:

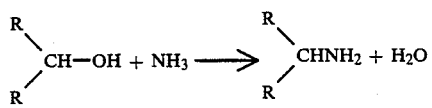

besides the desired primary amine there is generally also produced the secondary and sometimes the tertiary amine, since the initially produced primary amine can react further. Significant differences exist between different catalysts in their selectivity to primary amine and also in their productivities.

In order to improve selectivity and productivity a wide variety of promoters have been proposed in the patents literature. Representative of this literature may be mentioned U.S. Pat. Nos. 2,861,995 and 4,123,462, EP-A-0163253 and Australian patent application No. 33783/84. U.S. Pat. No. 2861995 describes the use in reductive amination of catalysts comprising one or more of nickel, cobalt, copper chromite, platinum and palladium, optionally supported on a carrier such as alumina. In U.S. Pat. No. 4,123,462 it is claimed that supported nickel/rhenium catalysts are particularly selective and have excellent activity. The disclosure of this patent mentions the possibility of adding other metals to nickel/rhenium catalysts but is only speculative as to the effect of such additions. Similar speculation is to be found in EP-A-0163253 which describes the use of supported nickel/iridium catalysts and claims high activity and selectivity for them. Australian patent application No. 33783/84 (corresponding to EP-A-0146508) discloses the use of a supported nickel/ruthenium catalyst and claims that it offers high selectivity in the production of ethylene diamine from monoethanolamine. No mention is made of the use of promoter metals. However, Examples are provided of catalysts incorporating first row transition metal components, but there is no indication that these are of any benefit and in fact the results reported in Table 2 could lead to the conclusion that they are detrimental.

We have now found an improved catalyst composition for use in reductive amination reactions.

Accordingly, the present invention provides a process for the production of an amine by reacting at elevated temperature a first reactant which is either an alcohol, an aldehyde or a ketone with a second reactant which is either ammonia, a primary or secondary amine or a nitrile in the presence as catalyst of a composition comprising (i) nickel, (ii) ruthenium, and (iii) at least one other transition metal selected from either the second or third row transition metals.

As regards the catalyst composition, any transition metal other than ruthenium may be used as component (iii). In the context of this specification the term 'transition metal' is defined as a metal having a partially filled 4d or 5d shell in at least one of its oxidation states. Suitable transition metals include palladium, rhenium and iridium, either individually or in combination.

Preferably, the catalyst composition is supported on a suitable support. Suitable supports include aluminas, silicas, silica-aluminas and carbons. A preferred support is gamma-alumina. Zeolites may also be used as supports.

As regards the relative proportions of components (i), (ii) and (iii) in the catalyst composition, the major component will generally be component (i), i.e. nickel, and components (ii), i.e. ruthenium, and (iii) i.e. transition metal(s) will be minor components. Thus, nickel may suitably form from 50 to 95% by weight of the catalyst composition and together ruthenium and transition metal may form the remainder of the composition. Typically the supported catalyst composition may contain about 10% nickel and 1% each of ruthenium and transition metal(s), the remainder of the composition being the support. However, higher nickel loadings may be used if desired.

The catalyst composition may be prepared by any of the methods conventionally employed for the production of catalysts, for example by precipitation or by impregnation. The supported composition is suitably prepared by an impregnation technique, which may be by co-impregnation or by sequential impregnation, preferably the latter. Impregnation techniques are well-known in the art and include both the incipient wetness technique and the excess solution technique.

A preferred process for producing a catalyst composition for use in the process of the present invention comprises the steps of (A) impregnating a support with a solution of a compound of nickel, (B) calcining the nickel compound present in the impregnated support obtained in step (A), (C) impregnating the impregnated support obtained in step (B) with a solution of a compound of a transition metal selected from either the second or third row transition metals, (D) impregnating the impregnated support obtained in step (C) with a solution of a compound of ruthenium, and (E) activating the composition obtained in step (D).

Optionally, after step (C), the catalyst may be contacted with either hydrogen or air at elevated temperature. The elevated temperature may suitably be in the range from 250° to 500° C., preferably from 250° to 350° C., for contact with hydrogen and from 500° to 600° C. for contact with air.

Suitable compounds of the metals include salts of the metals, for example the nitrates, halides and carboxylates. The compounds of the metals are used in the form of solutions thereof. Any suitable solvent may be employed for this purpose. A convenient solvent is water, though other solvents, such as for example alcohols, may be employed.

In step (B) of the process for producing the catalyst the compound of nickel present in the impregnated support obtained in step (A) is calcined. Calcination may suitably be accomplished at a temperature in the range from 550° to 600° C., typically about 580° C., though lower temperatures may be employed.

Activation (step E) may suitably be accomplished by heating the composition at elevated temperature, suitably greater than 280° C. in the presence of a reducing gas, for example hydrogen, for a period sufficient to activate the catalyst, typically for at least 3 hours and thereafter allowing the catalyst to cool in the presence of an inert gas, for example nitrogen. The activation step (step E) may be carried out as a further step in the preparative method, or may be carried out in the reductive amination reactor immediately prior to operation of the process of the invention, or both.

The catalyst, and in particular catalyst compositions comprising gamma-alumina supported nickel, ruthenium and either palladium, rhenium or iridium are highly effective in the production of primary amines by the reaction of an alcohol with ammonia because they can result in higher selectivities and/or productivities to primary amines than any of the known prior art catalysts.

In a particularly preferred embodiment therefore the present invention provides a process for the production of a primary amine which process comprises reacting an alcohol with ammonia at elevated temperature in the presence of a catalyst composition comprising (i) nickel, (ii) ruthenium and (iii) either palladium, rhenium or iridium on a gamma-alumina support.

The first reactant is preferably an alcohol. The alcohol may suitably be a monohydric alcohol, a dihydric alcohol or a polyhydric alcohol. Preferably the alcohol contains primary or secondary hydroxyl functions. Suitably the alcohol is an aliphatic or aromatic alcohol.

A preferred class of monohydric alcohols is the alkanols. Suitable alkanols are those of the formula:

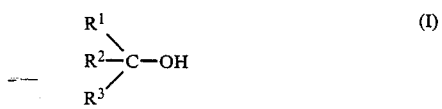

wherein
$R^1$ is hydrogen, and
$R^2$ and $R^3$ are independently either:
  (i) hydrogen, provided that the total number of carbon atoms in the alkanol does not exceed 30,
  (ii) aliphatic alkyl groups having from 1 to 30 carbon atoms, or
  (iii) alkyl groups bearing one or more functional groups.

Example of suitable functional groups in alternative (iii) include amine, amide and ether groups. Examples of suitable alkanols include ethanol, isopropanol, 1-triacontanol, monoethanolamine, 2-methoxyethanol and alkoxypolyalkylene glycols (provided that the total number of carbon atoms does not exceed 30). A suitable aromatic alcohol is benzyl alcohol.

Suitable diols are those of the formula:

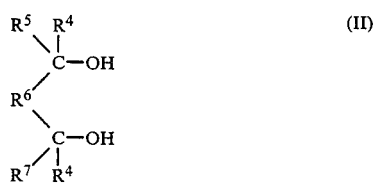

wherein
$R^4$ is hydrogen,
$R^5$ and $R^7$ are defined as for $R^2$ and $R^3$ in the formula (I), and
$R^6$ is defined as for alternatives (ii) and (iii) of $R^2$ and $R^3$ in the formula (I).

Examples of suitable diols include ethylene glycol, propylene glycol, butylene glycol, alkylene glycols, polyalkylene glycols, mixed polyalkylene glycols and their ether and polyether derivatives, provided that the total number of carbon atoms does not exceed 30.

Suitable polyhydric alcohols are those having more than two hydroxyl groups, each being attached to a carbon atom which is substituted as in the formula (II). Suitable examples of polyhydric alcohols include glycerol and triethanolamine.

Another preferred class of alcohol reactant is the polyether alcohols provided that in the cases of primay polyether alcohols and primary polyhydric polyether alcohols the total carbon numbers conform with the formulae (I) and (II). Examples include polyether monools, polyether diols and polyether polyols. The polyether amines which result from the use of such alcohols have a variety of uses, including the manufacture of polyureas.

The second reactant is preferably either ammonia or an amine.

Ammonia may be used in the form of anhydrous ammonia, liquid ammonia or in the form of a solution in a suitable solvent. Aqueous and anhydrous ammonia solutions which are available commercially on a large scale will be found convenient.

As regards the ratio of ammonia to alcohol useful in the performance of the invention, ratios greater than stoichiometric are suitable. The molar ratio of ammonia to alcohol may suitably be in the range from 1.5:1 to 20:1, though larger excesses may be used if desired. Higher ratios are preferred where practical because they favour increased selectivity to primary amine products.

Instead of ammonia there may be used an amine, which may be aromatic or aliphatic. Primary aliphatic amines are preferred. Although secondary amines may be employed, it is possible that they may react to produce products different from those desired. Amines containing from 1 to 30 carbon atoms are suitable. The use of a primary amine as the reactant provides a route for the production of secondary amines.

Aliphatic nitriles, for example acetonitrile, are also suitable reactants.

The process may be operated at a temperature in the range from 150° to 350° C., preferably in the range from 225° to 275° C.

The process may suitably be operated at pressures above autogenous pressure in the range from 150 psi to 1500 psi measured at ambient temperature, though lower and higher pressures above the autogenous pressure may be employed. A typical operating pressure is 750 psig above autogenous pressure.

It is preferred to apply a pressure above autogenous pressure in the reaction of an alcohol with ammonia using hydrogen because this is believed to have a beneficial effect on catalyst lifetime. Using other combinations of reactants, for example either an aldehyde or a ketone with ammonia, the presence of hydrogen is essential for the performance of the reaction. Optionally, pressure can be additionally applied using an inert gas, such as nitrogen.

The process may be operated batchwise or continuously, suitably employing the catalyst in the form of a slurry or fixed bed.

The process of the invention will now be further illustrated by reference to the following examples and comparison tests.

CATALYST PREPARATION

Vista Boehmite alumina was dried at 580° C. prior to use and was impregnated with a solution of nickel nitrate in water, sufficient to give a 10% w/w loading as nickel. Excess solvent was removed by rotary evaporation and the powder produced was calcined at 550° C. This stock, hereinbefore referred to as Catalyst A, was used to produce a range of promoted nickel catalysts by impregnation as follows:

|  | CATALYST | Transition Metal Source | Solvent | Second Metal Loading |
|---|---|---|---|---|
| 10% Ni + Pd | B | Pd (NO$_3$)$_2$ | water | 1% |
| 10% Ni + Ru | C | Ru Cl$_3$ 3H$_2$O | water | 0.2% |
| 10% Ni + Re | D | NH$_4$Re O$_4$ | water | 1% |
| 10% Ni + Ir | E | Ir Cl$_3$ | water | 0.5% |
| 10% Ni + Ru | F | RuCl$_3$3H$_2$O | water | 1% |

Third metals were then added to give:

|  | CATALYST | Transition Metal Source | Solvent | Second Metal Loading |
|---|---|---|---|---|
| 10% Ni/ 1% Pd + Ru | G | Ru Cl$_3$ 3H$_2$O | water | 0.84% |
| 10% Ni/0.2% Ru + Pd | H | Pd(NO$_3$)$_2$ H$_2$O | water | 0.92% |
| 10% Ni/1% Re + Ru | I | Ru Cl$_3$ 3H$_2$O | water | 1% |
| 10% Ni/0.5% Ir + Ru | J | Ru Cl$_3$ 3H$_2$O | water | 0.5% |
| 10% Ni/1% Ru + Ir | K | IrCl$_3$ | water | 1% |

Activation was performed prior to use, by heating the catalyst to greater than 280° C. in a stream of hydrogen for at least 3 hours and allowing the catalyst to cool in nitrogen. Catalyst surface areas were in the region of 140 m$^2$/g (Single Point B.E.T. Nitrogen adsorbtion). Catalyst C is equivalent to that described by Berol Kemi in Australian Pat. App 33783/84. Also prepared were a Ni/Re catalyst and a Ni/Ir catalyst following in all essential details the methods described by Union Carbide in U.S. No. 4123462 and EP 0163253 respectively. These catalysts are supported on GIRDLER support T-869 which is a silica alumina stated by Union Carbide to be a particularly active support material. These catalyst were used for comparison purposes, and were chosen because they would appear to exhibit the optimum combination of selectivity and productivity in the Examples of the Union Carbide patents.

EXAMPLES 1–3 AND COMPARISON TEST 1–4

These Examples and Comparison Tests demonstrate the high selectivity and high activity of the catalysts of the invention, and show them to be superior in these respects to prior art catalysts, in the conversion of isopropanol to isopropylamine.

Into a 70 ml magnetically stirred autoclave was placed 7.85 g (10 ml) of isopropanol and 30 ml of 0.880 specific gravity ammonia solution. A quantity of catalyst was placed in the autoclave (see Table 1) and the autoclave was connected to the gas manifold. The autoclave was pressurised to 750 psig using hydrogen and was then sealed. The autoclave was heated to 250° C. and maintained at this temperature for 3 hours (unless otherwise stated in Table 1) before being allowed to cool to room temperature. The contents were removed and analysed by Gas-liquid chromatography. Results are summarised in Table 1 Examples 1, 2 and 3 are with the catalysts of the invention. Comparison Tests 1, 2, 3 and 4 are with prior art catalysts.

TABLE 1

| Example | Catatlyst | Conversion (%) | Selectivity (%) isopropylamine | diisopropylamine | acetone | Productivity of primary amine/kg/kg catalyst/h | Wt. catalyst used. (g) |
|---|---|---|---|---|---|---|---|
| 1 | J | 36.3 | 99.7 | 0.3 | less than 0.1 | 1.47 | 0.55 |
| 2 | I | 66.2 | 94.6 | 1.8 | 3.6 | 4.10 | 0.40 |
| 3 | G | 12.4 | 99.7 | 0.3 | less than 0.1 | 0.59 | 0.55 |
| Comp Test 1 | C | 13.2 | 94.9 | 0.7 | 4.6 | 0.55 | 0.60 |
| Comp Test 2 | Ni/Ir/T869* | 9.0 | 92.0 | less than 0.1 | 8.0 | 0.54 | 0.40 |
| Comp Test 3 | Ni/Re/T869* | 18.2 | 98.1 | 0.3 | 1.4 | 0.34 | 1.38 |
| Comp Test 4 | Harshaw Ni 6458 | 5.6 | 96.6 | 0.2 | 3.4 | 0.24 | 0.60 |

*T869 is an alumina - silicate support produced by Girdler.

EXAMPLE 4 AND COMPARISON TESTS 5 AND 6

This Example and Comparison Tests 5 and 6 demonstrate the high selectivity shown by catalysts of the invention in the conversion of monoethanolamine to ethylenediamine.

Into a 70 ml magnetically stirred autoclave was placed 10.12 g (10 ml) of monoethanolamine and 30 ml of 0.880 specific gravity ammonia solution. A quantity of catalyst (see Table 2) was placed in the autoclave and the autoclave was then connected to the gas manifold. The autoclave was pressurised with 1000 psig of hydrogen and was then sealed. The autoclave was heated to 250° C. and maintained at this temperature for 8 hours before being cooled to room temperature. The contents were removed and analysed by gas liquid chromatography.

Results are summarised in Table 2.

TABLE 2

| Example | Catalyst | Quantity of Catalyst (g) | Conversion (%) | Selectivity to ethylenediamine (%) |
|---|---|---|---|---|
| 4 | I | 0.55 | 19.2 | 81.4 |
| Comp Test 5 | Ni/Re/T869 | 0.70 | 12.0 | 77.5 |
| Comp Test | C | 0.55 | 24.0 | 75.0 |

TABLE 2-continued

| Example | Catalyst | Quantity of Catalyst (g) | Conversion (%) | Selectivity to ethylenediamine (%) |
|---------|----------|--------------------------|----------------|------------------------------------|
| 6       |          |                          |                |                                    |

Comparison Tests 1–6 are not examples according to the present invention and are included only for comparison purposes.

EXAMPLES 5 AND 6 AND COMPARISON TESTS 7 TO 9

A 300 ml stainless steel autoclave was charged with 2 g of catalyst, 110 g polyether polyol CP-1 (having a molecular weight of about 4800 and having three secondary hydroxyl functions, ex BPCL, Lavera) and 10 mls propylamine. Once sealed the autoclave was pressurised to 220 psig with hydrogen. The reaction mixture was then heated at 230° C. for 8 hours.

Following the reaction, the product was separated and decanted to remove the catalyst. Unreacted propylamine was removed under vacuum. The resulting viscous product was analysed by assessing the reduction of the hydroxyl peak in the $^{13}$Cnmr spectrum.

The catalysts used and the results obtained are given in Table 3.

Comparison Tests 7 to 9 are not examples according to the present invention because they lack at least one essential catalyst component. They are included only for the purpose of comparison.

TABLE 3

| Example     | Catalyst | Catalyst Composition        | Degree of amination $^{13}$C nmr (%) |
|-------------|----------|-----------------------------|---------------------------------------|
| Comp Test 7 | A        | 10% Ni/gamma-alumina        | less than 5                           |
| Comp Test 8 | D        | 10% Ni/1% Re/gamma-alumina  | 7                                     |
| Comp Test 9 | F        | 10% Ni/1% Ru/gumma-alumina  | 13                                    |
| 5           | I        | 10% Ni/1% Ru/1% Re/gamma-alumina | 23                               |
| 6           | K        | 10% Ni/1% Ir/1% Ru/gamma-alumina | 19                               |

The polyether amines so-produced are mixed products resulting mainly from amination by propylamine with minor amounts derived from amination by ammonia.

We claim:

1. A process for the production of an amine by reacting at elevated temperature a first reactant which is an alcohol with a second reactant which is either ammonia or a primary or secondary amine in the presence as catalyst of a composition comprising (i) nickel, (ii) ruthenium, and (iii) at least one other transition metal selected from the group consisting of palladium, rhenium and iridium.

2. A process according to claim 1 wherein the catalyst is supported.

3. A process according to claim 2 wherein the support is gamma-alumina.

4. A process according to claim 1 where nickel (component (i) of the catalyst) forms from 50 to 95% by weight based on the total weight of the components (i) to (iii).

5. A process according to claim 1 wherein the alcohol is an alkanol of the formula (I).

6. A process according to claim 1 wherein the alcohol is an amino alcohol.

7. A process according to claim 1 wherein the alcohol is a diol of the formula (II).

8. A process according to claim 1 wherein the alcohol is a polyether polyol.

9. A process according to claim 1 wherein the first reactant is an alcohol the second reactant is ammonia and a pressure above the autogenous pressure is applied using hydrogen.

10. A process as defined in claim 1 wherein the catalyst composition comprises nickel, ruthenium and rhenium.

11. A process as defined in claim 1 wherein the catalyst composition comprises nickel, ruthenium and iridium.

12. A process for the production of a primary amine which process comprises reacting an alcohol with ammonia at elevated temperature in the presence of a catalyst composition comprising (i) nickel, (ii) ruthenium and (iii) either palladium, rhenium or iridium on a gamma-alumina support.

13. A process for the production of a secondary amine which process comprises reacting an alcohol with a primary amine at elevated temperature in the presence of a catalyst composition comprising (i) nickel, (ii) ruthenium, and (iii) either palladium, rhenium or iridium on an alumina support.

* * * * *